United States Patent
Enomoto

(10) Patent No.: US 9,650,357 B2
(45) Date of Patent: May 16, 2017

(54) REAGENT FOR ENHANCING GENERATION OF CHEMICAL SPECIES

(71) Applicant: TOYO GOSEI CO., LTD., Ichikawa-shi, Chiba (JP)

(72) Inventor: Satoshi Enomoto, Kamagaya (JP)

(73) Assignees: Toyo Gosei Co., Ltd., Ichikawa-shi, Chiba (JP); Osaka University, Suita-shi, Osaka (JP)

( * ) Notice: Subject to any disclaimer, the term of this patent is extended or adjusted under 35 U.S.C. 154(b) by 0 days.

(21) Appl. No.: 14/392,352

(22) PCT Filed: Jun. 23, 2014

(86) PCT No.: PCT/JP2014/003369
§ 371 (c)(1),
(2) Date: Dec. 23, 2015

(87) PCT Pub. No.: WO2014/208076
PCT Pub. Date: Dec. 31, 2014

(65) Prior Publication Data
US 2016/0194300 A1    Jul. 7, 2016

Related U.S. Application Data

(60) Provisional application No. 61/838,751, filed on Jun. 24, 2013.

(51) Int. Cl.
*C07D 335/16* (2006.01)
*G03F 7/00* (2006.01)
(Continued)

(52) U.S. Cl.
CPC ............ *C07D 335/16* (2013.01); *C07C 33/24* (2013.01); *C07C 35/38* (2013.01); *C07C 35/40* (2013.01); *C07C 43/23* (2013.01); *C07C 49/83* (2013.01); *C07D 219/06* (2013.01); *C07D 309/12* (2013.01); *C07D 311/86* (2013.01); *G03F 7/0045* (2013.01); *G03F 7/0382* (2013.01); *G03F 7/0392* (2013.01); *G03F 7/16* (2013.01); *G03F 7/2051* (2013.01); *G03F 7/36* (2013.01);
(Continued)

(58) Field of Classification Search
None
See application file for complete search history.

(56) References Cited

U.S. PATENT DOCUMENTS

| | | | |
|---|---|---|---|
| 4,347,111 A | 8/1982 | Gehlhaus et al. | |
| 4,721,734 A | 1/1988 | Gehlhaus et al. | |

(Continued)

FOREIGN PATENT DOCUMENTS

| | | |
|---|---|---|
| JP | 53-144539 | 12/1978 |
| JP | 4-165359 | 6/1992 |

(Continued)

OTHER PUBLICATIONS

Application for U.S. Patent, U.S. Appl. No. 14/392,352, sharing common inventors, available on the U.S. Patent Office website.
(Continued)

*Primary Examiner* — Shamim Ahmed
(74) *Attorney, Agent, or Firm* — TraskBritt P.C.

(57) ABSTRACT

A reagent that enhances acid generation of a photoacid generator and composition containing such reagent is disclosed.

13 Claims, 1 Drawing Sheet

(51) Int. Cl.

| | | |
|---|---|---|
| *H01L 21/027* | (2006.01) | |
| *H01L 21/308* | (2006.01) | |
| *G03F 7/004* | (2006.01) | |
| *G03F 7/038* | (2006.01) | |
| *G03F 7/039* | (2006.01) | |
| *C07C 33/24* | (2006.01) | |
| *C07C 35/38* | (2006.01) | |
| *C07C 35/40* | (2006.01) | |
| *C07C 43/23* | (2006.01) | |
| *C07C 49/83* | (2006.01) | |
| *C07D 219/06* | (2006.01) | |
| *C07D 309/12* | (2006.01) | |
| *C07D 311/86* | (2006.01) | |
| *G03F 7/16* | (2006.01) | |
| *G03F 7/20* | (2006.01) | |
| *G03F 7/36* | (2006.01) | |

(52) U.S. Cl.
CPC ...... *H01L 21/0271* (2013.01); *H01L 21/3081* (2013.01); *C07C 2103/18* (2013.01); *C07C 2103/24* (2013.01)

(56) References Cited

U.S. PATENT DOCUMENTS

| | | | |
|---|---|---|---|
| 6,171,755 | B1 | 1/2001 | Elian et al. |
| 6,177,229 | B1 | 1/2001 | Saito et al. |
| 7,851,252 | B2 | 12/2010 | Nealey et al. |
| 9,017,930 | B2 * | 4/2015 | Nakamura ................ G03F 7/40 430/322 |
| 2006/0269879 | A1 | 11/2006 | Elian et al. |
| 2011/0250540 | A1 * | 10/2011 | Huang .................. G03F 7/2022 430/296 |
| 2012/0040288 | A1 * | 2/2012 | Adams .................. G03F 7/0045 430/270.1 |
| 2015/0060728 | A1 | 3/2015 | Enomoto et al. |
| 2015/0099893 | A1 | 4/2015 | Enomoto |
| 2015/0140493 | A1 | 5/2015 | Enomoto et al. |
| 2015/0241779 | A1 | 8/2015 | Enomoto |
| 2016/0070165 | A1 | 3/2016 | Enomoto |

FOREIGN PATENT DOCUMENTS

| | | |
|---|---|---|
| JP | 07-239547 | 9/1995 |
| JP | 10293396 | 11/1998 |
| JP | 11-231542 | 8/1999 |
| JP | 11282167 | 10/1999 |
| JP | 2002311586 | 10/2002 |
| JP | 2004101819 | 4/2004 |
| JP | 2005284322 | 10/2005 |
| JP | 2008-543033 | 11/2008 |
| JP | 2010151999 | 7/2010 |
| JP | 2012168526 | 9/2012 |
| JP | 2013211479 | 1/2014 |
| WO | 2006125509 | 11/2006 |
| WO | 2014129556 | 8/2014 |
| WO | 2014208076 | 12/2014 |

OTHER PUBLICATIONS

Application for U.S. Patent, U.S. Appl. No. 14/392,350, sharing common inventors, available on the U.S. Patent Office website.
Application for U.S. Patent, U.S. Appl. No. 14/909,051, sharing common inventors, available on the U.S. Patent Office website.
Application for U.S. Patent, U.S. Appl. No. 14/392,348, sharing common inventors, available on the U.S. Patent Office website.
Application for U.S. Patent, U.S. Appl. No. 14/912,027, sharing common inventors, available on the U.S. Patent Office website.
Application for U.S. Patent, U.S. Appl. No. 15/025,518, sharing common inventors, available on the U.S. Patent Office website.
Application for U.S. Patent, U.S. Appl. No. 15/026,745, sharing common inventors, available on the U.S. Patent Office website.
Application for U.S. Patent, U.S. Appl. No. 15/027,855, sharing common inventors, available on the U.S. Patent Office website.
PCT International Search Report dated Sep. 30, 2014, PCT/JP2014/03369.
Seiji Nagahara et al., Methods to Improve Radiation Sensitivity an Chemically Amplified Resists by Using Chain Reactions of Acid Generation, Advances in Resist Technology and Processing XVII, 2000, pp. 386-394, vol. 3999, Proceedings of SPIE.

* cited by examiner

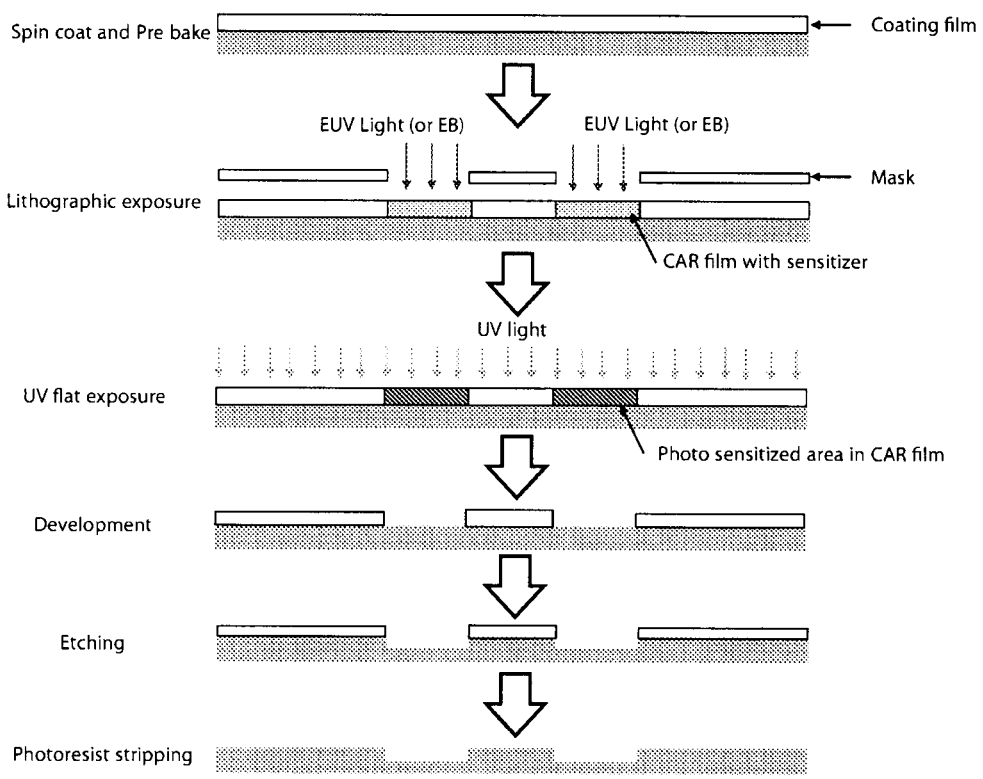

REAGENT FOR ENHANCING GENERATION OF CHEMICAL SPECIES

CROSS-REFERENCE TO RELATED APPLICATIONS

This application is a national phase entry under 35 U.S.C. §371 of International Patent Application PCT/JP2014/003369, filed Jun. 23, 2014, designating the United States of America and published in English as International Patent Publication WO 2014/208076 A1 on Dec. 31, 2014, which claims the benefit under Article 8 of the Patent Cooperation Treaty and under 35 U.S.C. §119(e) to U.S. Provisional Patent Application Ser. No. 61/838,751, filed Jun. 24, 2013, the disclosure of each of which is hereby incorporated herein in its entirety by this reference.

TECHNICAL FIELD

Several aspects of this disclosure relate to the fields of a reagent enhancing a generation of a chemical species such as acid and base. An intermediate formed from such reagent can function as a photosensitizer and also enhances generation of a chemical species.

BACKGROUND

Current high-resolution lithographic processes are based on chemically amplified resists (CARs) and are used to pattern features with dimensions less than 100 nm.

A method for forming pattern features with dimensions less than 100 nm is disclosed in U.S. Pat. No. 7,851,252 (filed on Feb. 17, 2009), the entire contents of which are incorporated herein by this reference.

BRIEF SUMMARY

A reagent that enhances generation of a chemical species and a composition are disclosed herein. Typically, such reagent assists the generation of Bronsted acid or base from a precursor. Furthermore, such reagent can apply to the generation of Lewis acid and base. Typically, such reagent generates an intermediate such as ketyl radical having a reducing character and the intermediate enhances a generation of acid from the precursor. In other words, such reagent functions as an acid generation enhancer (AGE).

The intermediate is converted to a product functioning as a photosensitizer. After formation of such product, an irradiation of the product results in its excited state, which can transfer energy or an electron to the precursor, or accept energy or an electron from the precursor. The precursor generates the chemical species after receiving the energy or the electron or donating the energy or the electron. Since several examples of AGEs are required to high electron donor character to enhance electron transfer to the precursor, such AGEs have at least one electron donating group on the aromatic ring such as alkoxy group and hydroxyl group. A reaction of the chemical species with a compound results in decomposition of the compound and regeneration of the chemical species. In other words, such reagent enhances generation of the chemical species in chemically amplified fashion, even if excitation means is altered in a set of processes.

A typical example for such AGE reagents is methanol containing an aryl group. For example, a composition containing the reagent, a precursor that is to form a chemical species, and a compound that is to react with the chemical species can be applied as photoresist to manufacturing of electronic devices such as a semiconductor device and an electro-optical device. For example, after a coating film of the composition is exposed to an extreme ultraviolet (EUV) light and an electron beam (EB) in a first step, the coating film can be exposed to a light of which intensity is higher than that of the EUV light or the EB such as an UV light and a visible light. The composition can be applied to a chemically amplified reaction involved with a photoacid generator (PAG) and a resin containing a protective group such as an ester and ether group, which is to decompose by reacting with a chemical species such as acid generated from the PAG.

An oxidation reaction of aryl methanol, which is a typical AGE, easily occurs to form a corresponding carbonyl compound. To attain the long-term stability of such AGE, the hydroxyl group of the AGE is preferably protected by a protective group such as a tetrahydropyranyl group, an ester group, and an ether group.

In certain embodiments relating to an aspect of this disclosure, a reagent is characterized by: an intermediate that is to be generated from the reagent; an intermediate that is capable of enhancing a generation of a chemical species from a precursor; and a product resulting from the intermediate that has a conjugation length longer than a conjugation length of the reagent.

In certain embodiments relating to this disclosure, a reagent is characterized by: an intermediate that is to be generated from the reagent; an intermediate that is capable of enhancing a generation of a chemical species from a precursor; and a product resulting from the intermediate that has a level of a highest occupied molecular orbital (HOMO) higher than a level of a highest occupied molecular orbital (HOMO) of the reagent.

With regard to any one of the above reagents, it is preferred that a reaction of the chemical species with a first compound or the precursor is to regenerate the chemical species.

With regard to any one of the above reagents, it is preferred that the intermediate is to be generated from the reagent by a feed of energy to the reagent or an acceptor receiving the energy.

With regard to any one of the above reagents, it is preferred that the intermediate has a reducing character.

With regard to any one of the above reagents, it is preferred that the intermediate is a radical.

With regard to any one of the above reagents, it is preferred that the intermediate discharges at least one of a hydrogen atom and a hydrogen ion that have reducing characters.

An example of such intermediate is a ketyl radical, which can easily discharge a hydrogen atom.

An example of such chemical species is acid or base.

With regard to any one of the above reagents, it is preferred that the feed of the energy is carried out by a first irradiation of the reagent with at least one of a light of which wavelength is equal to or shorter than 15 nm and an electron beam (EB).

With regard to any one of the above reagents, it is preferred that the feed of the energy is carried out by a first irradiation of the reagent with a first light of which wavelength is a first wavelength or an electron beam; and a second irradiation of the product is capable of enhancing generation of a chemical species from a precursor.

With regard to any one of the above reagents, it is preferred that the feed of the energy is carried out by a first irradiation of the reagent with a first light of which wavelength is a first wavelength or an electron beam; and a second irradiation of the product with a second light is capable of enhancing generation of the chemical species from the precursor.

With regard to any one of the above reagents, it is preferred that a first wavelength of the first light is shorter than a second wavelength of the second light.

In certain embodiments relating to an aspect of this disclosure, a composition includes any one of the above reagents and the precursor.

With regard to the composition, it is preferred that the composition further includes the first compound.

With regard to the composition, it is preferred that the first compound is capable of reacting with the chemical species.

With regard to the composition, it is preferred that a second irradiation of the product is capable of enhancing a generation of the chemical species from the precursor.

With regard to the composition, it is preferred that the second irradiation is carried out by a second light of which wavelength is equal to or longer than 100 nm.

With regard to the composition, it is preferred that the second irradiation is carried out by a light of which wavelength is equal to or longer than 300 nm.

With regard to the composition, it is preferred that the product functions as a sensitizer for the second irradiation.

With regard to the composition, it is preferred that the product is capable of being excited by the second irradiation to form an excited state of the product; and the precursor is capable of generating the chemical species by receiving an electron from the excited state of the product.

With regard to the composition, it is preferred that the product is capable of being excited by the second irradiation to form an excited state of the product; the precursor is capable of generating the chemical species by receiving an electron from the excited state of the product; and a reaction of the first compound with the chemical species is capable of occurring while the reaction is accompanied with a regeneration of the chemical species.

In certain embodiments relating to an aspect of this disclosure, a composition includes: a reagent represented by one of formula (I), and a precursor that can function as a generation source of acid.

Chem. 1

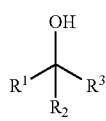

(I)

In formula (I), it is preferred that $R^1$ is a hydrogen atom; $R^2$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than a carbon atom and a hydrogen atom; and $R^3$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than a carbon atom and a hydrogen atom.

With regard to the composition, it is preferred that $R^2$ is connected to $R^3$ through at least one bond.

With regard to the composition, it is preferred that at least one of $R^2$ and $R^3$ is an aromatic group.

With regard to the composition, it is preferred that the product is formed by oxidation of the intermediate.

In certain embodiments relating to an aspect of this disclosure, a composition includes a reagent and a precursor that can generate acid by accepting an energy or at least one hydrogen atom. It is preferred that the reagent includes: a hydroxyl group; a first cyclic moiety that contains a carbon atom bonded to the hydroxyl group and a hydrogen atom; and an intermediate formed from the reagent that is converted into the product.

With regard to the composition, it is preferred that the reagent further includes a second cyclic moiety and the first cyclic moiety contains at least two atoms that are also contained in the second cyclic moiety.

In certain embodiments relating to an aspect of this disclosure, a composition includes a reagent represented by one of formula (II) and a precursor that function as a generation source of acid.

Chem. 2

(II)

In formula (II), it is preferred that $R^1$ is a hydrogen atom; $R^2$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than a carbon atom and a hydrogen atom; $R^3$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than a carbon atom and a hydrogen atom; and $R^4$ is a protective group for a hydroxyl group.

In certain embodiments relating to an aspect of this disclosure, a composition includes a reagent represented by one of formula (III) and a precursor that can function as a generation source of acid.

Chem. 3

(III)

In formula (III), it is preferred that $R^1$ is a hydrogen atom; $R^2$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than a carbon atom and a hydrogen atom; $R^3$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than a carbon atom and a hydrogen atom; and $R^4$ is a group containing a carbon atom.

With regard to the composition, it is preferred that $R^4$ is one of an ester group, an alkyl group and a tetrahydropyranyl group.

With regard to any one of the above reagents, it is preferred that the reagent is a group that is to be deprotected by acid or base.

With regard to any one of the above compositions, it is preferred that the reagent contains a group that is to be deprotected by a chemical species formed from the precursor.

In certain embodiments relating to an aspect of this disclosure, a method for manufacturing a device is carried out by using any one of the compositions.

In certain embodiments relating to an aspect of the disclosure, a method includes: applying a solution of the composition to a substrate such that a coating film including the composition is formed on the substrate; a first irradiating of the coating film with at least one of a first electromagnetic ray and a first particle ray such that a first portion of the coating film is irradiated with the at least one of the electromagnetic ray and the particle ray while a second portion of the coating film is not irradiated with the at least one of the electromagnetic ray and the particle ray; a second irradiating of the coating film with at least one of a second electromagnetic ray and a second particle ray; removing the first portion; and etching the substrate such that a third portion of the substrate on which the first portion has been present is etched.

With regard to the method, it is preferred that: the first electromagnetic ray of which wavelength is a first wavelength; the second electromagnetic ray of which wavelength is a second wavelength; and the first wavelength is shorter than the second wavelength.

With regard to the method, it is preferred that the first wavelength is equal to or shorter than 15 nm.

With regard to the method, it is preferred that the first wavelength is equal to or shorter than 15 nm and the second wavelength is equal to or longer than 300 nm.

With regard to the method, it is preferred that the second irradiating is carried out without a mask.

In certain embodiments relating to an aspect of this disclosure, any one of the above methods is carried out by using an apparatus.

BRIEF DESCRIPTION OF THE DRAWINGS

In the drawings, which illustrate what is currently considered to be the best mode for carrying out the disclosure:

The FIGURE shows fabrication processes of a device such as an integrated circuit (IC) using photoresist including an acid-generation enhancer.

DETAILED DESCRIPTION

Experimental Procedures

Synthesis of 2,4-dimethoxy-4'-methoxybenzophenone 2.00 g of 2,4-dihydroxy-4'-hydroxybenzophenone, 1.95 g of dimethyl sulfate and 2.14 g of potassium carbonate are dissolved in 16.0 g of acetone. The mixture is stirred at reflux temperature for 8 hours. Since then, the mixture is cooled to 25 degrees Celsius and further stirred after addition of 80.0 g of water, then extracted with 20.0 g ethyl acetate and the organic phase is washed with water. Thereafter, ethyl acetate is distilled away, and the resultant is purified by silica gel column chromatography (ethyl acetate: hexane=3:97). Thereby, 1.43 g of 2, 4-dimethoxy-4'-methoxybenzophenone is obtained.

Synthesis of (2,4-dimethoxyphenyl)-(4'-methoxyphenyl)-methanol

Example 1

1.0 g of 2,4-dimethoxy-4'-methoxybenzophenone and 0.01 g of potassium hydroxide are dissolved in 12.0 g of methanol. 0.42 g of sodium boron hydride is added to the methanol solution. The mixture is stirred at reflux temperature for 3 hours. Since then, the mixture is added to the 80 g of water, then extracted with 20.0 g ethyl acetate and the organic phase is washed with water. Thereafter, ethyl acetate is distilled away. Thereby, 0.90 g of (2,4-dimethoxyphenyl)-(4'-methoxyphenyl)-methanol is obtained.

Chem. 4

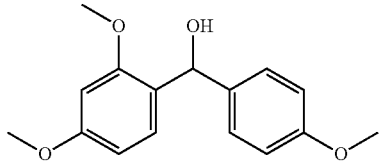

Example 1

A solution containing 5.0 g of α-methacryloyloxy-γ-butylolactone, 6.03 g of 2-methyladamantane-2-methacrylate, and 4.34 g of 3-hydroxyadamantane-1-methacrylate, 0.51 g of dimethyl-2,2'-azobis(2-methylpropionate), and 26.1 g of tetrahydrofuran is prepared. The prepared solution is added for 4 hours to 20.0 g of tetrahydrofuran placed in flask with stirring and boiling. After the addition of the prepared solution, the mixture is heated to reflux for 2 hours and cooled to room temperature. Addition of the mixture by drops to a mixed liquid containing 160 g of hexane and 18 g of tetrahydrofuran with vigorous stirring precipitates the copolymer. The copolymer is isolated by filtration. Purification of the copolymer is carried out by vacuum drying following two washings by 70 g of hexane, and thereby 8.5 g of white powder of the copolymer is obtained.

Chem. 5

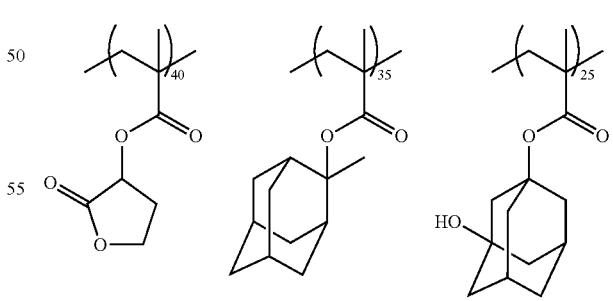

Resin A

Preparation of Samples for Evaluation (The "Evaluation Sample")

The Evaluation Samples are prepared by dissolving 23.5 mg of (2,4-dimethoxyphenyl)-(4'-methoxyphenyl)-methanol, 600 mg of resin A and 24.9 mg of diphenyliodonium nonafluorobutanesulfonate as a photoacid generator (PAG) in 8000 mg of cyclohexanone.

Evaluation of Sensitivity

Before applying each of the Evaluation Samples to an Si wafer, hexamethyldisilazane (HMDS, Tokyo Chemical Industry) is spin-coated at 2000 rpm for 20 seconds on the surface of the Si wafer and baked at 110 degrees Celsius for 1 minute. Then, each of the Evaluation Samples is spin-coated on the surface Si wafers that have been treated with HMDS at 2000 rpm for 20 seconds to form a coating film. The prebake of the coating film is performed at 110 degrees Celsius for 60 seconds. Then, the coating film of the Evaluation Sample is exposed to an extreme ultraviolet (EUV) output from an EUV light source. After the EUV light exposure, an irradiation of the coating film with a UV light is carried out at an ambient condition. After the UV light exposure, a post-exposure-bake (PEB) is carried out at 100 degrees Celsius for 60 seconds. The coating film is developed with NMD-3 (tetra-methyl ammonium hydroxide 2.38%, Tokyo Ohka Kogyo) for 60 seconds at 25 degrees Celsius and rinsed with deionized water for 10 seconds. The thickness of the coating film measured using film thickness measurement tool is approximately 150 nm.

A sensitivity ($E_0$ sensitivity) is evaluated by measuring the dose size to form a pattern constituted by 2 μm lines where the thickness of the coating film is not zero and 2 μm spaces where the thickness of the coating film is zero using 30 keV EBL system JSM-6500F (JEOL, beam current: 12.5 pA, <1E-4 Pa) with Beam Draw (Tokyo Technology) and the UV exposures using FL-6BL (bright line is mainly from 320 nm to 380 nm, Toshiba).

Even if the UV exposure is carried out without a mask, 2 μm spaces are formed in the parts of the coating film that have been exposed to the EUV light. This indicates that a product functioning as a photosensitizer for the UV light is generated in the parts exposed to the EUV light.

Table 1 shows the dose sizes corresponding to $E_0$ sensitivities measured for Evaluation Samples 1 to 4. Table 1 indicates that the doses of the UV exposure for $E_0$ sensitivity decreases with increase of the doses of the EUV light exposure.

TABLE 1

The doses for $E_0$ light by an EUV light and UV exposure for the Evaluation Samples

| | Total dose for $E_0$ | |
| --- | --- | --- |
| | EUV dose [μC/cm²] | UV dose [mJ/cm²] |
| Run 1 | 20.0 | 0 |
| Run 2 | 13.8 | 560 |
| Run 3 | 8.8 | 1100 |
| Run 4 | 3.8 | 3350 |

Each of Examples 2, 3, 4, and 5 are also preferably used as AGE instead of (2,4-dimethoxyphenyl)-(4'-methoxyphenyl)-methanol. Each of the Examples is converted into a corresponding ketone that can function as a photosensitizer after an EUV light or electron beam exposure.

Chem. 6

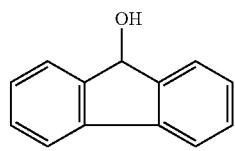

Example 2

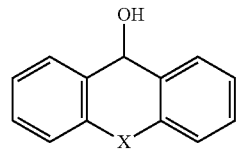

Example 3

X = CH², NH, O, or S

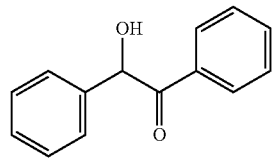

Example 4

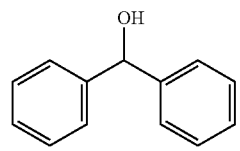

Example 5

Examples 1-5 are also protected by a protective group such as tetrahydropyranyl and ester.

Synthesis of bis-(4-methoxyphenyl) methanol 2.0 g of 4,4'-dimethoxybenzohenone and 0.02 g of potassium hydroxide are dissolved in 16.0 g of methanol. 0.94 g of sodium boronhydride is added to the methanol. The mixture is stirred at reflux temperature for 3 hours. Since then, the mixture is added to the 80 g of water, then extracted with 20.0 g of ethyl acetate and the organic phase is washed with water. Thereafter, ethyl acetate is distilled away. Thereby, 1.79 g of bis-(4-methoxyphenyl)methanol is obtained.

Synthesis of 2-[Bis-(4-methoxy-phenyl)-methoxy]-tetrahydro-pyran

Example 6

Chem. 7 Synthesis of 2-[Bis-(4-methoxy-phenyl)-methoxy]-tetrahydro-pyran (Example 6)

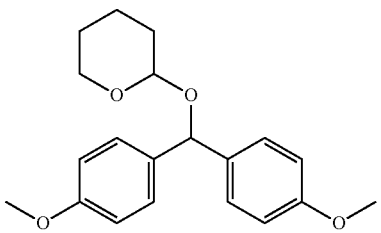

Example 6

2.75 g of 2H-dihydropyran and 0.74 g of pyridinium p-toluenesulfonate are dissolved in 30.0 g of methylene chloride. 2.0 g of bis-(4-methoxyphenyl)methanol dissolved by 8.0 g of methylene chloride is added dropwise to the mixture containing 2H-dihydropyran and pyridinium p-toluenesulfonate over 30 minutes. After that, the mixture is stirred at 25 degrees Celsius for 3 hours. Since then, the mixture is further stirred after addition of 3% aqueous solution of sodium carbonate, then extracted with 20.0 g of ethyl acetate and the organic phase is washed with water. Thereafter, ethyl acetate is distilled away. Thereby, 1.99 g of 2-[Bis-(4-methoxy-phenyl)-methoxy]-tetrahydro-pyran is obtained.

Preparation of Evaluation Samples 5 and 6

Evaluation Sample 5 is prepared by dissolving 300 mg of resin A, 36.7 mg of diphenyliodonium nonafluorobutane-sulfonate as a photoacid generator (PAG), and 13.7 mg of coumarin 6 as an indicator in 2000 mg of cyclohexanone.

Evaluation Sample 6 is prepared by dissolving 14.1 mg of 2-[Bis-(4-methoxy-phenyl)-methoxy]-tetrahydro-pyran, 300 mg of resin A, 36.7 mg of 4,4'-di-(t-butyphenyl)iodonium nonafluorobutanesulfonate as a PAG, and 13.7 mg of coumarin 6 as an indicator in 2000 mg of cyclohexanone.
Evaluation of Efficiency of Acid Generation Films are formed on 4-inch quartz wafers by spin-coating of Evaluation Samples 5 and 6. Each of the films is irradiated with EUV light, of which volumes are 0, 10, 20, 30, and 40 $\mu C/cm^2$ output by an EUV light lithography apparatus. Subsequent to the EUV light irradiations, the efficiencies for the films are obtained by plotting absorbances at 534 nm and each of the films are assigned to quantities of protonated coumarin 6 generated by the respective volumes of EUV.

Table 2 shows the relative acid-generation efficiencies for the Evaluation Samples 5 and 6. In Table 2, the acid-generation efficiency for the Evaluation Sample 5 is used as a benchmark. The results shown in Table 2 indicate that the acid-generation efficiency is improved by the reduction of the photoacid generator by ketyl radical formed from 2-[Bis-(4-methoxy-phenyl)-methoxy]-tetrahydro-pyran. This indicates that the tetrahydropyranyl group of 2-[Bis-(4-methoxy-phenyl)-methoxy]-tetrahydro-pyran is cleaved by generated acid by exposure of an EUV light and bis-(4-methoxyphenyl)methanol is generated.

TABLE 2

The relative acid-generation efficiencies for the Evaluation Samples 5 and 6

| | Relative acid-generation efficiency |
|---|---|
| Evaluation Sample 5 | 1.0 |
| Evaluation Sample 6 | 1.1 |

As understood from the results, a reactive intermediate having reducing character that is protected by an acid-dissociable group is also considered to enhance the efficiency of acid generation.

A reaction of Example 6 with acid results in a corresponding alcohol. The corresponding alcohol is oxidized to a corresponding ketone, which can act as a photosensitizer. Therefore, if an irradiation with a light of which wavelength is longer than 220 nm is carried out after exposure to a solution containing Example 6 and a PAG to EUV light or electron beam, the efficiency of acid generation is further enhanced.

A photoresist including Example 6 as AGE obtained by the processes by the above procedures can be applied to fabrication processes of a device, such as an integrated circuit (IC).

The FIGURE shows fabrication processes of a device such as an integrated circuit (IC) using a photoresist including the acid generation enhancer (AGE) obtained by the processes by the above procedures.

A silicon wafer is provided. The surface of a silicon wafer is oxidized by heating the silicon wafer in the presence of oxygen gas.

A solution of a chemically amplified composition (CAR) including an AGE, resin A, and a PAG is applied to the surface of an Si wafer by spin coating to form a coating film. The coating film is prebaked.

An irradiation of the coating film with an EUV light through a mask is carried out after prebake of the Si wafer. The deprotection reaction of resin A is induced by acid generated by photoreaction of the photoacid generator and assistance by AGE.

An electron beam can be used instead of the EUV light.

After the EUV irradiation of the coating film, an irradiation of the coating film with a light of which wavelength is equal to or longer than 300 nm is carried out without any mask.

Development of the coating film that has been irradiated with the EUV light and the light of which wavelength is equal to or longer than 300 nm is performed after the prebake.

The coating film and the silicon wafer are exposed to plasma. After that, the remaining film is removed.

An electronic device such as an integrated circuit is fabricated utilizing the processes shown in the FIGURE. The deterioration of the device due to the irradiation with a light is suppressed, compared to existing photoresists since times for irradiation of the coating film is shortened.

AGEs can be bound to a polymer chain. For example, at least each of a mother moiety of Examples 1-6 can be a polymer chain through an ether group or an ester group.

The invention claimed is:
1. A composition, comprising:
   a reagent;
   a first compound able to react with a chemical species to cause a deprotection reaction of the first compound; and
   a precursor,
   wherein the reagent is selected from the group consisting of a first reagent, a second reagent, and a third reagent, the first reagent being represented by one of formula (I),

(I)

wherein
   $R^1$ is a hydrogen atom;
   $R^2$ is a phenyl group, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom; and
   $R^3$ is a hydrogen atom, a phenyl group, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom, the second reagent being represented by one of formula (II),

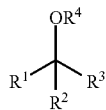

(II)

wherein
- $R^1$ is a hydrogen atom;
- $R^2$ is a phenyl group, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom;
- $R^3$ is a hydrogen atom, a phenyl group, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom; and
- $R^4$ is a protective group for a hydroxyl group or a group containing a carbon atom; and the third reagent includes a hydroxyl group and a first cyclic moiety that contains a carbon atom bonded to the hydroxyl group and a hydrogen atom;

wherein:
an intermediate is generated from the reagent by a feed energy;
the intermediate enhances a generation of the chemical species from a precursor;
a product resulting from the intermediate has a conjugation length longer than a conjugation length of the reagent;
wherein the feed energy is carried out by a first irradiation of the reagent or an acceptor receiving the energy with at least one of a light, the wavelength of which is shorter than or equal to 15 nm and an electron beam; and
wherein the generation of the chemical species from the precursor is improved by a second irradiation with a light, the wavelength of which is longer than or equal to 300 nm.

2. The composition according to claim 1, wherein a reaction of the chemical species with a first compound or the precursor regenerates the chemical species.

3. The composition according to claim 1, wherein the intermediate has a reducing character.

4. The composition according to claim 1, wherein the intermediate is a radical.

5. The composition according to claim 1, wherein the intermediate discharges at least one of a hydrogen atom and hydrogen ion that have reducing characters.

6. The composition according to claim 1, wherein the intermediate is a ketyl radical.

7. The composition according to claim 1, wherein the chemical species is acid.

8. The composition according to claim 1, wherein $R^2$ is connected to $R^3$ through at least one bond.

9. The composition according to claim 1, wherein at least one of $R^2$ and $R^3$ is an aromatic group.

10. The composition according to claim 1, wherein the product is formed by oxidation of the intermediate.

11. The composition according to claim 1, wherein:
the reagent further includes a second cyclic moiety; and
the first cyclic moiety contains at least two atoms which are also contained in the second cyclic moiety.

12. The composition according to claim 1, wherein $R^4$ is one of an ester group, alkyl group and tetrahydropyranyl group.

13. A method for manufacturing a device, the method comprising:
applying a solution of the composition according to claim 1 to a substrate such that a coating film including the composition is formed on the substrate;
a first irradiating the coating film with at least one of a first electromagnetic ray and a first particle ray such that a first portion of the coating film is irradiated with the at least one of the electromagnetic ray and the particle ray while a second portion of the coating film is not irradiated with the at least one of the electromagnetic ray and the particle ray;
a second irradiating the coating film with at least one of a second electromagnetic ray and a second particle ray;
removing the first portion; and
etching the substrate such that a third portion of the substrate on which the first portion has been present is etched.

* * * * *